(12) United States Patent
Weck et al.

(10) Patent No.: US 8,071,389 B2
(45) Date of Patent: Dec. 6, 2011

(54) METHOD FOR CONTROLLING HYDROGENATION

(75) Inventors: Alexander Weck, Freinsheim (DE);
Markus Rösch, Dienheim (DE);
Gunther Windecker, Ludwigshafen (DE); Gunnar Heydrich, Kirchenstr (DE); Rolf Pinkos, Bad Dürkheim (DE);
Olga Schubert, Ludwigshafen (DE);
Klaus Harth, Tai Tam (CN)

(73) Assignee: BASF Aktiengesellschaft (DE)

( * ) Notice: Subject to any disclaimer, the term of this patent is extended or adjusted under 35 U.S.C. 154(b) by 675 days.

(21) Appl. No.: 11/815,125

(22) PCT Filed: Jan. 30, 2006

(86) PCT No.: PCT/EP2006/050507
§ 371 (c)(1),
(2), (4) Date: Jul. 31, 2007

(87) PCT Pub. No.: WO2006/082165
PCT Pub. Date: Aug. 10, 2006

(65) Prior Publication Data
US 2008/0166816 A1    Jul. 10, 2008

(30) Foreign Application Priority Data
Feb. 1, 2005 (DE) .......................... 10 2005 004 604

(51) Int. Cl.
*G01N 33/00* (2006.01)

(52) U.S. Cl. .......................... 436/144; 73/23.2; 73/19.01
(58) Field of Classification Search .................. 436/144; 73/19.01, 23.2
See application file for complete search history.

(56) References Cited

U.S. PATENT DOCUMENTS

| | | | | | |
|---|---|---|---|---|---|
| 3,541,178 | A | * | 11/1970 | Gottfried | 585/262 |
| 3,653,842 | A | | 4/1972 | Putman | |
| 3,798,002 | A | | 3/1974 | Putman | |
| 3,809,621 | A | | 5/1974 | Putman | |
| 4,083,809 | A | * | 4/1978 | De Thomas et al. | 502/245 |
| 4,476,094 | A | * | 10/1984 | Carson | 422/62 |
| 2005/0119494 | A1 | * | 6/2005 | Fischer et al. | 548/554 |

FOREIGN PATENT DOCUMENTS

| | | |
|---|---|---|
| DE | 102 09 633 A1 * | 9/2003 |
| JP | 51-020527 B | 6/1976 |

* cited by examiner

*Primary Examiner* — Christine T Mui
(74) *Attorney, Agent, or Firm* — Connolly Bove Lodge & Hutz LLP

(57) ABSTRACT

The invention relates to a method of controlling a hydrogenation of a starting material in a hydrogenation reactor, in which the amount of hydrogen reacted in the hydrogenation is firstly determined, the ratio of the amount of hydrogen reacted to the amount of starting material fed in is then derived, this ratio is compared with a prescribed value and, finally, at least one process parameter is altered if the ratio of the amount of hydrogen reacted to the amount of starting material fed in deviates by a prescribed amount from the prescribed value.

19 Claims, 3 Drawing Sheets

METHOD FOR CONTROLLING HYDROGENATION

RELATED APPLICATIONS

This application is a national stage application (under 35 U.S.C. 371) of PCT/EP2006/050507 filed Jan. 30, 2006 which claims benefit of German application 10 2005 004604.5 filed Feb. 1, 2005.

The invention relates to a method of controlling a hydrogenation of a starting material in a hydrogenation reactor.

Hydrogenations are generally carried out at a hydrogen partial pressure of from 5 to 400 bar. The hydrogen consumed during the hydrogenation has to be continually replaced. This is effected by introduction of hydrogen from a reservoir via a regulator. The pressure in the reservoir is higher than the system pressure. The regulator is generally a regulating valve.

To control the amount of hydrogen which has to be supplied to the hydrogenation process, two different methods are used at present. In one method, the pressure in the system is measured and is kept constant by means of a regulator which acts directly or indirectly, via a cascade regulation, on the supply device for the hydrogen. This is referred to as supply-side pressure regulation. In the second method of controlling the amount of replacement hydrogen, a fixed amount of hydrogen is fed into the system and the system pressure is kept constant by means of a regulator which acts on the offgas valve of the gas circuit. This is referred to as offgas-side pressure regulation.

A disadvantage of the control method known from the prior art is that effects on the process and knock-on effects from the process are taken into account only unsatisfactorily. In particular, effects of the pressure on the hydrogenation result are not taken into account. Thus, for example, an increase in pressure can, depending on the hydrogenation to be carried out, lead to overhydrogenation or underhydrogenation. Overhydrogenation means that the desired product produced by the hydrogenation reacts with hydrogen in the reactor and an undesirable by-product is thus formed. Underhydrogenation means that less product is produced from the same amount of starting material.

In the case of the currently used methods of control in the hydrogenation, this means that, for example, in the event of a temperature increase in the hydrogenation reaction accompanied by a resulting increase in the degree of overhydrogenation, the set value of the pressure regulation has to be altered manually in order to compensate the influence of the temperature increase.

It is an object of the invention to provide a method of controlling a hydrogenation which requires no manual adjustment of process parameters.

This object is achieved by a method of controlling a hydrogenation of a starting material in a hydrogenation reactor, which comprises the following steps;
a) determination of the amount of hydrogen reacted in the hydrogenation,
b) determination of the ratio of the amount of hydrogen reacted to the amount of starting material fed in,
c) comparison of the ratio derived in step b) with a prescribed value and
d) alteration of at least one process parameter if the ratio derived in step b) deviates by a prescribed amount from the prescribed value.

The determination of the ratio of the amount of hydrogen reacted to the amount of starting material fed in results in a constant product quality being obtained, since it ensures that an approximately equal amount of hydrogen always reacts with a particular amount of starting material. In this way, overhydrogenation or underhydrogenation is avoided.

The process parameter in step d), which is altered if the ratio of the amount of hydrogen reacted to the amount of starting material fed in deviates by a prescribed amount from a prescribed value, is, for example, the temperature of the pressure in the hydrogenation reactor or the amount of hydrogen fed in.

The prescribed value with which the ratio of the amount of hydrogen reacted to the amount of starting material fed in is compared is dependent on the pressure and the temperature in the hydrogenation reactor and also on the desired hydrogenation product.

The amount of hydrogen reacted in the hydrogenation is preferably derived from the difference between the amount of hydrogen discharged from the process and the amount of hydrogen fed into the process. To determine the amount of hydrogen fed into the process, a flow meter is preferably installed on the inflow line to the hydrogenation reactor through which the hydrogen is introduced. Suitable methods of measuring the flow are volumetric methods, differential pressure methods, inductive methods and ultrasound methods, pressure sensors and also thermal sensors. Volumetric methods used for measuring the flow are, for example, volume meters such as oval wheel meters or turbine meters, flow measurement by means of differential pressure methods is carried out using orifice plates, nozzles or Venturi tubes, and pressure sensors are, for example, Pitot tubes or Prandtl's Pitot tubes. Suitable thermal sensors are, for example, hot wire anemometers. However, the flow measurement can also be carried out using any other method known to those skilled in the art.

The amount of hydrogen discharged from the process is preferably measured in an offgas line through which unreacted reaction gases are discharged. Here too, the amount of hydrogen is preferably determined by means of a flow meter. Suitable measurement methods are the same methods as for the flow measurement for determining the amount of hydrogen fed in.

The gases discharged through the offgas line are preferably recirculated to the process as recycle gas.

In a preferred embodiment, a product separator in which the hydrogenation product is separated off from unreacted reaction gases is installed downstream of the hydrogenation reactor. The offgas line via which the unreacted reaction gases are discharged leads from the product separator. To separate the hydrogenation product from the unreacted reaction gases, the mixture leaving the hydrogenation reactor is cooled in at least one heat exchanger so that the hydrogenation product condenses out. A liquid/gas phase separation is then carried out in the product separator.

In a preferred embodiment, a set value for a temperature regulator is generated from the comparison of the ratio of the amount of hydrogen reacted to the amount of starting material fed in with a prescribed value, and the temperature regulator regulates the temperature in the hydrogenation reactor. Since the degree of hydrogenation is dependent on the temperature, the desired product quality is achieved via the temperature in the hydrogenation reactor with the aid of the amount of hydrogen reacted based on starting material. Overhydrogenation or underhydrogenation is avoided.

The pressure in the hydrogenation reactor is regulated on the feed side or offgas side as in the methods known from the prior art. In the case of feed-side pressure regulation, the pressure in the system is measured and kept constant by means of a regulator which acts directly or indirectly by means of a cascade regulation on the supply device for the hydrogen. The supply device for the hydrogen is preferably a regulating valve.

In the case of offgas-side regulation, the pressure in the system is likewise measured and kept constant by means of a regulator which acts on an offgas valve in the offgas line.

In a preferred embodiment, the ratio of hydrogen reacted to amount of starting material fed in is kept constant by adjusting the amount of hydrogen fed in. Furthermore, the pressure established in the hydrogenation reactor is kept constant by regulating the temperature by comparing the pressure established in the hydrogenation reactor with a prescribed pressure in a regulator and generating a regulating parameter for the temperature via the deviation of the actual value from the prescribed value.

To keep constant the ratio of hydrogen reacted to amount of starting material fed in by adjustment of the amount of hydrogen fed in, the flow cross section in a regulator valve which regulates the amount of hydrogen fed in is increased or decreased by the regulator in which the ratio of the amount of hydrogen reacted to the amount of starting material fed in is derived when this ratio deviates from a prescribed value. For this purpose the regulating valve is opened further as a function of a setting parameter which is transmitted from the regulator in which the ratio of the amount of hydrogen reacted to the amount of starting material fed in is derived to the regulating valve when more hydrogen is required, or closed further when less hydrogen is required. The flow cross section in the regulating valve is increased or decreased by the opening or closing motion of the regulating valve so that more or less hydrogen flows through it.

It is possible to keep the pressure in the hydrogenation reactor constant by regulating the temperature in the hydrogenation reactor because the ratio of the amount of hydrogen reacted to the amount of starting material fed in changes when there is a change in the pressure at a prescribed pressure and a prescribed temperature, leading to a change in the degree of hydrogenation and thus to a temperature change in the hydrogenation reactor. As a result of a temperature change, the intended degree of hydrogenation is restored, which leads to the prescribed ratio of the amount of hydrogen reacted to the amount of starting material fed in being restored and this in turn leads to the pressure in the hydrogenation reactor changing so that the prescribed pressure is restored.

In a further embodiment, both the ratio of hydrogen reacted to amount of starting material fed in and the temperature in the hydrogenation reactor are kept constant. No regulation of the pressure in the hydrogenation reactor is carried out. This is possible when the hydrogenation activity is so strongly dependent on the system pressure that the system has only one possible operating point at a constant temperature. In this case, the system is self-regulating in respect of the pressure. The desired degree of hydrogenation is established as a function of the ratio of the amount of hydrogen reacted to the amount of starting material fed in. As soon as the consumption of hydrogen in the hydrogenation reactor is lower than the amount fed in, the system pressure rises as a result of the accumulation of hydrogen. As a result, the activity of the catalyst increases and, in addition, the residence time in the hydrogenation reactor increases because of the increased gas density. This in turn leads to an increase in the reaction rate. The reaction rate increases until the amount of hydrogen fed in once again corresponds to the amount of hydrogen reacted. Conversely, if the amount of hydrogen reacted is greater than the amount of hydrogen fed in, the system pressure drops as a result of the decreasing content of hydrogen in the hydrogenation reactor. This leads to a reduction in the activity of the catalyst and at the same time to a reduction in the residence time in the reactor. The reduction in the activity of the catalyst results in a decrease in the reaction rate. The reaction rate decreases until the amount of hydrogen reacted and the amount of hydrogen fed in are again equal.

In a preferred embodiment, the temperature in the hydrogenation reactor is adjusted via the temperature of a heat transfer medium. The heat transfer medium preferably flows through at least the one tube located in the reactor and/or through a reactor wall, configured as a double wall. In a preferred embodiment, the hydrogenation reactor is configured as a shell-and-tube heat exchanger. Here, the heat transfer medium flows around the tubes and the reaction mixture flows through the tubes.

Depending on the temperature at which the hydrogenation is carried out, suitable heat transfer media are, for example, water, heat transfer oils or salt melts.

When water is used as a transfer medium, the pressure of the water is preferably selected so that the water vaporizes as a result of heat uptake from the exothermic hydrogenation.

In a preferred embodiment, the hydrogenation is carried out in the presence of a heterogeneous catalyst. As active component, the catalyst preferably comprises Cu, Pt, Rh, Pd or mixtures thereof. The catalyst can, for example, have been installed in the reactor as woven fabric, knitted fabric, ordered packing, packing elements or granules, which in each case comprise(s) the active component. The woven fabric, knitted fabric, ordered packing, packing elements or granules can be made of the active component, comprise the active component as, for example, constituent of an alloy or be coated with the active component. It is also possible to coat the reactor wall with the active component.

When a reactor in the form of a shell-and-tube heat exchanger is used, the catalyst is preferably installed as woven fabric, knitted fabric, ordered packing or bed of packing elements in the individual tubes of the shell-and-tube heat exchanger.

In a preferred embodiment, the hydrogenation reactor comprises at least one vapor phase and/or at least one liquid phase or a supercritical fluid. The hydrogenation reactor preferably comprises at least one vapor phase in which the hydrogenation occurs.

In a preferred embodiment, the feed stream comprises one or more compounds selected from among maleic acid, maleic anhydride, maleic (mono)esters and further maleic anhydride derivatives. The hydrogenation converts these compounds comprised in the feed stream into one or more compounds selected from among succinic acid, succinic anhydride, γ-butyrolactone, butanediol, tetrahydrofuran and butanol.

The hydrogenation is preferably carried out at a pressure in the range from 5 to 100 bar, particularly preferably in the range from 5 to 30 bar. The temperature in the hydrogenation is preferably in the range from 170° C. to 300° C. and particularly preferably in the range from 200° C. to 280° C.

In the hydrogenation of maleic acid, maleic anhydride, maleic (mono)esters and/or further maleic anhydride derivatives, the ratio of the amount of hydrogen reacted to the amount of starting material fed in is preferably selected so that when the hydrogenation is carried out at a pressure in the range from 5 to 30 and a temperature in the range from 200° C. to 280° C. in the gas phase, a product comprising from 0 to 80% of γ-butyrolactone, from 20 to 100% of tetrahydrofuran and not more than 10% of by-products is formed. By-products formed in this hydrogenation are, for example, butanol, succinic anhydride, succinic acid or butane.

The invention is illustrated below with the aid of a drawing. In the drawing.

In the following, identical reference numerals denote the same components.

Figure 1:
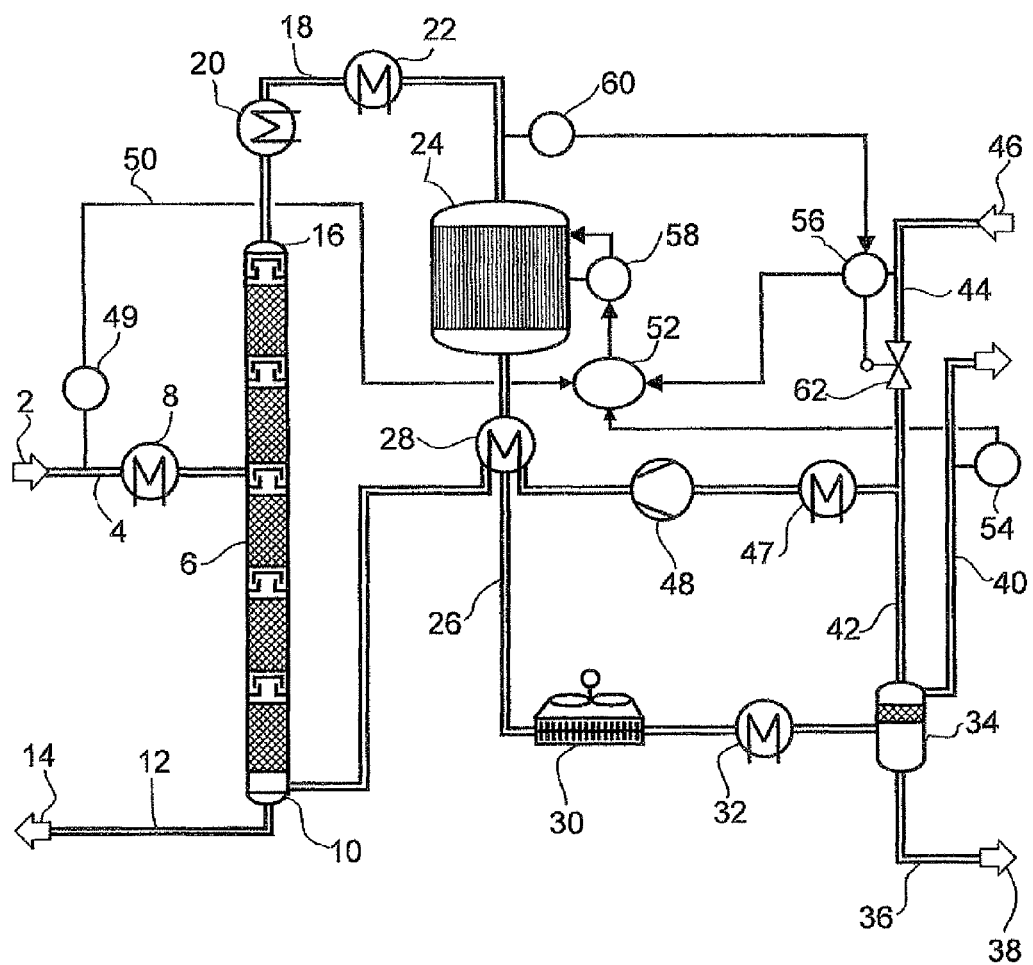
FIG. 1 shows a first embodiment of a control system for a hydrogenation.

For the hydrogenation, starting material is fed to the process at a starting material inlet 2. For this purpose, the starting material is preferably dissolved in a solvent. The mixture of starting material and solvent flows via a feed line 4 into a column 6. A first heat exchange 8 in which the mixture of starting material and solvent is preheated is installed in the feed line 4.

In the column 6, the preheated mixture of starting material and solvent is separated into starting material and solvent. The separation is preferably carried out by distillation. To separate the mixture of starting material and solvent, internals are preferably comprised in the column. Suitable internals are, for example, trays such as bubble-cap trays, sieve trays, tunnel-cap trays or other trays known to those skilled in the art, or packing such as packing elements, beds of packing, ordered packing, or formed-loop or drawn-loop knitted fabrics.

Preheated hydrogen is fed in at the bottom 10 of the column 6. The heat necessary to separate starting material and solvents is introduced into the column 6 via the preheated hydrogen. The gaseous hydrogen flows from the bottom 10 to the top 16 of the column 6 and at the same time transfers heat to the mixture of starting material and solvent, with the lower-boiling components vaporizing from this mixture and thus being separated from the higher-boiling components.

At the bottom 10 of the column 6, the solvent is conveyed via a solvent offtake line 12 to a solvent offtake 14.

The solvent separated off in the column 6 is, in a preferred embodiment, reused for dissolving the starting material. For this purpose, the solvent can be worked up before reuse if impurities are still comprised in the solvent.

The starting material separated off in the column 6 is taken off together with the hydrogen at the top 16 of the column 6. Starting material and hydrogen flow via a connecting line 18 firstly into a partial condenser 20, from there into a preheater 22 and finally into a hydrogenation reactor 24.

In the partial condenser 20, the vapor stream which leaves the top 16 of the column 6 and comprises starting material and hydrogen is cooled, resulting in part of the vapor stream condensing. As a result, mainly components whose boiling point is above the boiling point of the starting material and are still comprised in the vapor stream are condensed out. The substances condensed out in the partial condenser 20 flow back into the column 6. The still vaporous stream comprising starting material and water is then heated in the preheater 22 to the temperature necessary for the hydrogenation. The hydrogenation occurs in the hydrogenation reactor 24.

In the embodiment shown in FIG. 1, the hydrogenation reactor is in the form of a shell-and-tube heat exchanger. A heterogeneous catalyst comprising Cu, Pt, Rh, Pd or mixtures thereof as active component is preferably comprised in the tubes of the hydrogenation reactor 24. The catalyst is preferably present in the form of a woven fabric, drawn-loop knitted fabric, ordered packing or as packing elements.

Apart from the embodiment shown here, in which the reactor is configured as a shell-and-tube heat exchanger, it is also possible to use a tube reactor, a fluidized-bed reactor or in the other reactor which is known to those skilled in the art and is suitable for hydrogenations.

A product-containing gas stream is discharged from the hydrogenation reactor 24 via an offtake line 26. The product-containing gas stream flows firstly through a second heat exchanger 28 in which it transfers heat to the hydrogen-containing gas stream fed to the bottom 10 of the column 6. As a result, cooling of the product-containing gas stream occurs. In at least one product condenser, at least the product is condensed from the product-containing gas stream. As product condensers, it is possible to use, for example, air-cooled condensers 30 or condensers 32 which are supplied with any desired liquid or gaseous heat transfer medium. Particularly suitable heat transfer media are liquid heat transfer media which vaporize as a result of the heat uptake in the condenser 32. Water which is just at the boiling point under reduced pressure is very particularly suitable.

The offtake line 26 in which the product condensers 30, 32 are installed opens into a product separator 34. In the product separator 34, the liquid product is separated from gaseous constituents. The liquid product goes via a product offtake line 36 to a product offtake 38.

A hydrogen-containing offgas stream is discharged via an offgas line 40 at the top of the product separator 34. The hydrogen-containing offgas stream is preferably reused as recycled gas for replacing the hydrogen reacted in the hydrogenation in the hydrogenation reactor 24.

A hydrogen-containing gas stream is likewise taken off via a second line 42 which is likewise located at the top of the product separator 34. A hydrogen line 44 via which hydrogen from a hydrogen inlet 46 is introduced opens into the line 42. The amount of the via the hydrogen line 44 preferably corresponds to the amount of hydrogen reacted in the hydrogenation reactor 24. In a particularly preferred embodiment, the hydrogen which has been taken from the process via the offgas line 40 is recirculated to the process via the hydrogen line 44 after an optional work-up.

The hydrogen-containing gas stream taken off from the product separator 34 via the line 42 and the additional hydrogen fed in via the hydrogen line 44 are heated in a third heat exchanger 47, compressed to system pressure in a compressor 48 and subsequently heated further in the second heat exchanger 28 by heat uptake from the gaseous product stream which has been taken off from the hydrogenation reactor 24. The hydrogen-containing gas stream which has been preheated in this way is then conveyed to the bottom 10 of the column 6.

To control the hydrogenation, the amount of starting material flowing through the feed line 4 is measured by means of a first flow meter 49. The value measured by the first flow meter 49 is transmitted via a data line 50 to a regulator 52.

The amount of hydrogen-containing gas leaving the process via the offgas line 40 is measured by means of a second flow meter 54. This measured value is likewise transmitted to the regulator 52. The amount of hydrogen fed to the process is measured by means of a flow regulator 56. For this purpose the flow regulator 56 is located on the hydrogen line 44. The measured value from the flow regulator 56 is likewise transmitted to the regulator 52. In the regulator 52, the difference between the measured values from the second flow meter 54 and from the flow regulator 56 is derived and divided by the measured value from the first flow meter 49. This ratio is compared with a prescribed value and thus gives a set point which is transmitted to a temperature regulator 58. The temperature in the hydrogenation reactor 24 is set by means of the temperature regulator 58. The temperature is preferably regulated here by means of the temperature and the volume flow of the heat transfer medium flowing through the hydrogenation reactor 24.

The system pressure in the connecting line 18 leading to the hydrogenation reactor 24 is measured by means of a pressure regulator 60. This measured value is transmitted as setting parameter to the flow regulator 56. The flow regulator 56 acts on a regulating valve 62 which is located in the hydrogen line 44. The amount of hydrogen to be fed into the process is adjusted by means of the regulating valve 62.

Figure 2:
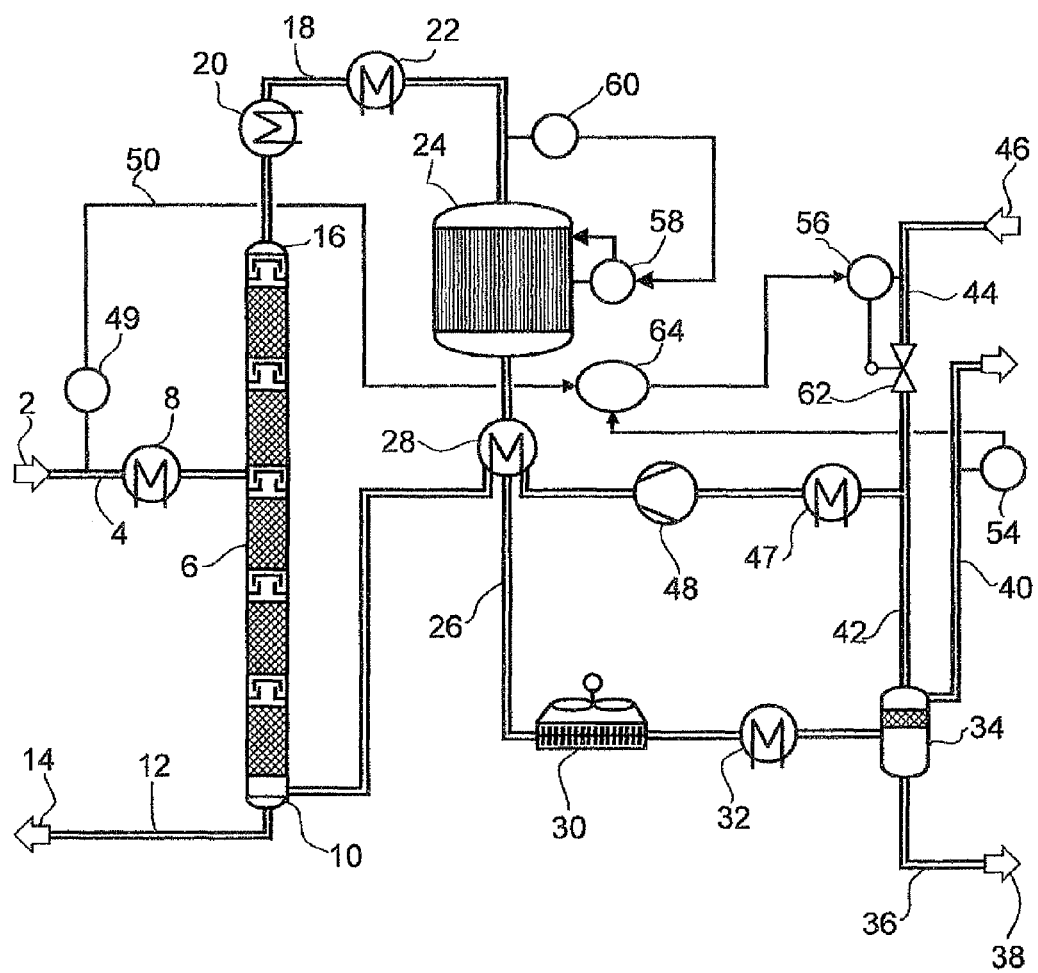
FIG. 2 shows a second embodiment of a control system for a hydrogenation and FIG. 3 shows a third embodiment of a control system for a hydrogenation.

FIG. 2 shows a second embodiment of a control system for a hydrogenation.

The embodiment shown in FIG. 2 differs from that shown in FIG. 1 only in the way in which the hydrogenation is controlled. In the embodiment shown in FIG. 2, the value measured by the first flow meter 49 is transmitted to a regulator 64. The regulator 64 also receives the value measured by the second flow meter 54.

The objective of the regulating system shown in FIG. 2 is to keep constant the ratio of the amount of hydrogen reacted to the amount of starting material. For this purpose, the amount of hydrogen to be fed in is derived in the regulator 62 from the ratio of the amount of hydrogen reacted to the amount of starting material. This value is transmitted as setting parameter to the flow regulator 56. The flow regulator 56 sends a setting signal to the regulating valve 62 by means of which the amount of hydrogen to be fed in is set. In this way, the ratio of the amount of hydrogen reacted to the amount of starting material fed in is kept constant.

In the embodiment shown in FIG. 2, too, the pressure regulator 60 measures the pressure in the connecting line 18 before this opens into the hydrogenation reactor 24. The pressure regulator 60 provides a setting parameter for the temperature regulator 58 by means of which the temperature in the hydrogenation reactor 24 is set. In this way, the operating point at which the best hydrogenation result is obtained is set in the hydrogenation reactor 24. The operating point is defined by pressure, temperature and the ratio of the amount of hydrogen reacted to the amount of starting material fed in.

Figure 3:
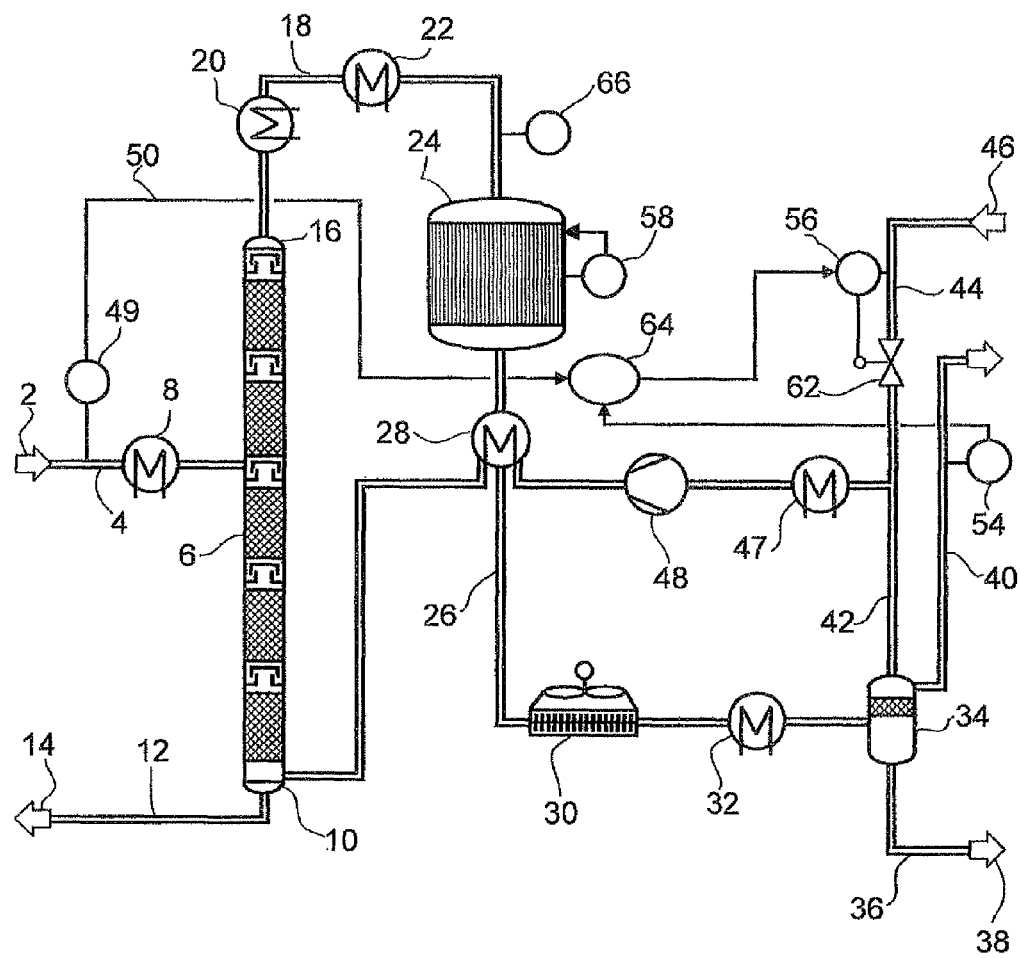

FIG. 3 shows a third embodiment of a control system for a hydrogenation.

The embodiment shown in FIG. 3 differs from that shown in FIG. 2 in that the temperature in the hydrogenation reactor 24 is kept constant and the pressure in the system sets itself. For this purpose, a pressure meter 66 by means of which the pressure in the system is measured is installed only in the connecting line 18.

The temperature is kept constant by measuring the temperature in the hydrogenation reactor 24 by means of the temperature regulator 58 and setting the temperature and the flow of the heat transfer medium on the basis of the temperature measurement.

In the embodiment shown in FIG. 3, too, the ratio of the amount of hydrogen reacted to the 35 amount of starting material fed in is kept constant, as in the embodiment shown in FIG. 2, for which purpose the measured values from the first flow meter 49 and the second flow meter 54 are sent to the regulator 64 and the amount of hydrogen to be fed in is sent as setting parameter by the regulator 64 to the flow regulator 56. The amount of hydrogen to be fed in is set by means of the regulating valve 62 which receives a setting parameter from the flow regulator 56.

REFERENCE NUMERALS

2 Starting material inlet
4 Feed line
6 Column
8 First heat exchanger
10 Bottom
12 Solvent offtake line
14 Solvent offtake
16 Top
18 Connecting line
20 Partial condenser
22 Preheater
24 Hydrogenation reactor
26 Offtake line
28 Second heat exchanger
30 Air-cooled condenser
32 Condenser
34 Product separator
36 Product offtake line
38 Product offtake
40 Offgas line
42 Line
44 Hydrogen line
46 Hydrogen inlet
47 Heat exchanger
48 Compressor
49 First flow meter
50 Data line
52 Regulator
54 Second flow meter
56 Flow regulator
58 Temperature regulator
60 Pressure regulator
62 Regulating valve
64 Regulator
66 Pressure meter

The invention claimed is:

1. A method of controlling a hydrogenation of a starting material in a hydrogenation reactor, which comprises the following steps:
    a) determining the amount of hydrogen reacted in the hydrogenation,
    b) determining the ratio of the amount of hydrogen reacted to the amount of starting material fed in,
    c) comparing the ratio derived in step b) with a prescribed value and
    d) altering at least one process parameter if the ratio derived in step b) deviates by a prescribed amount from the prescribed value.

2. The method of claim 1, wherein the amount of hydrogen reacted is derived from the difference between the amount of hydrogen discharged from the process and the amount of hydrogen fed into the process.

3. The method of claim 1, wherein a set point for a temperature regulator which regulates the temperature in the hydrogenation reactor is generated from the comparison carried out in step c).

4. The method of claim 3, wherein the hydrogenation reactor a pressure is kept constant by means of a feed-side or discharge-side pressure regulation.

5. The method of claim 1, wherein the ratio of hydrogen reacted to amount of starting material fed in is kept constant by adjusting the amount of hydrogen fed in and the pressure established in the hydrogenation reactor is kept constant by regulating the temperature by comparing the pressure established in the hydrogenation reactor with a prescribed pressure in a regulator and generating a regulating parameter for the temperature via the deviation of the actual value from the prescribed value.

6. The method of claim 1, wherein both the ratio of hydrogen reacted to amount of starting material fed in and the temperature in the hydrogenation reactor are kept constant.

7. The method of claim 1, wherein the hydrogenation reactor a temperature is set by means of the temperature of a heat transfer medium.

8. The method of claim 7, wherein the heat transfer medium flows through at least one tube located in the hydrogenation reactor and through a reactor wall configured as a double wall.

9. The method of claim 7, wherein the heat transfer medium flows through at least one tube located in the hydrogenation reactor or through a reactor wall configured as double wall.

10. The method of claim 1, wherein the hydrogenation is carried out in the presence of a heterogeneous catalyst.

11. The method of claim 10, wherein the catalyst comprises Cu, Pt, Rh, Pd or mixtures thereof as active components.

12. The method of claim 1, wherein the hydrogenation reactor comprises at least one vapor phase and at least one liquid phase or a supercritical fluid.

13. The method of claim 1, wherein the starting material fed in of the hydrogenation reactor comprises one or more compounds selected from the group consisting of maleic acid, maleic anhydride, maleic (mono)esters and maleic anhydride derivatives, and one or more of the compounds selected from the group consisting of succinic acid, succinic anhydride, γ-butyrolactone, butanediol, tetrahydrofuran and butanol.

14. The method of claim 1, wherein the hydrogenation is carried out at a temperature in the range from 170 to 300° C. and at a pressure in the range from 5 to 100 bar.

15. A method of controlling a hydrogenation of a starting material in a hydrogenation reactor, which comprises the following steps:
   a) determining the amount of hydrogen reacted in the hydrogenation,
   b) determining the ratio of the amount of hydrogen reacted to the amount of starting material fed in,
   c) comparing the ratio derived in step b) with a prescribed value and
   d) altering at least one process parameter if the ratio derived in step b) deviates by a prescribed amount from the prescribed value and
   wherein the process parameter being altered is the temperature or the pressure in the hydrogenation reactor or the amount of hydrogen fed in.

16. The method as claimed in claim 15, wherein the process parameter being altered is the temperature.

17. The method as claimed in claim 16, wherein the process parameter being altered is the pressure in the hydrogenation reactor.

18. The method as claimed in claim 16, wherein the process parameter being altered is the amount of hydrogen fed in.

19. The method as claimed in claim 16, wherein the process parameter being altered is the temperature or the pressure in the hydrogenation reactor or the amount of hydrogen fed in.

* * * * *